US011833302B2

(12) United States Patent
Bender, II et al.

(10) Patent No.: US 11,833,302 B2
(45) Date of Patent: *Dec. 5, 2023

(54) ANESTHESIA VAPORIZER RESERVOIR AND SYSTEM

(71) Applicant: General Electric Company, Schenectady, NY (US)

(72) Inventors: Thomas Bender, II, Madison, WI (US); Joseph Lacey, Waukesha, WI (US); Russell Kuzelka, Madison, WI (US); David Wahl, Madison, WI (US)

(73) Assignee: General Electric Company, Schenectady, NY (US)

( * ) Notice: Subject to any disclaimer, the term of this patent is extended or adjusted under 35 U.S.C. 154(b) by 133 days.

This patent is subject to a terminal disclaimer.

(21) Appl. No.: 17/358,846

(22) Filed: Jun. 25, 2021

(65) Prior Publication Data

US 2021/0322694 A1    Oct. 21, 2021

Related U.S. Application Data

(63) Continuation of application No. 15/793,740, filed on Oct. 25, 2017, now Pat. No. 11,077,268.

(51) Int. Cl.
*A61M 16/01*    (2006.01)
*A61M 16/00*    (2006.01)
(Continued)

(52) U.S. Cl.
CPC ........ *A61M 16/01* (2013.01); *A61M 16/0057* (2013.01); *A61M 16/0093* (2014.02);
(Continued)

(58) Field of Classification Search
CPC .... A61M 16/0057–0084; A61M 16/01; A61M 16/10–1095; A61M 12/127;
(Continued)

(56) References Cited

U.S. PATENT DOCUMENTS 4,161,308 A  *  7/1979  Bell ..................... F04B 9/125
                                                      251/303
4,438,305 A      3/1984  Johnson
                (Continued)

FOREIGN PATENT DOCUMENTS

DE        19954097       5/2000
EP         2645070      10/2013
                (Continued)

*Primary Examiner* — Valerie L Woodward
*Assistant Examiner* — Paige Kathleen Bugg
(74) *Attorney, Agent, or Firm* — ANDRUS INTELLECTUAL PROPERTY LAW, LLP (57) ABSTRACT

An anesthesia vaporizer system includes a vaporizer reservoir forming a sump chamber that contains liquid anesthetic agent and a fill chamber isolated from the sump chamber configured to receive liquid anesthetic agent from a refill container. A piston is in the sump chamber configured to maintain a constant force on the liquid anesthetic agent in the sump chamber, and a transfer valve is configured to permit the liquid anesthetic agent to flow from the fill chamber to the sump chamber. The vaporizer reservoir has an outlet port that delivers the liquid anesthetic agent from the sump chamber to a vaporizing system that vaporizes the liquid anesthetic agent for delivery to a patient.

21 Claims, 10 Drawing Sheets

(51) Int. Cl.
 *A61M 16/18* (2006.01)
 *A61M 16/10* (2006.01)

(52) U.S. Cl.
 CPC ........... *A61M 16/183* (2013.01); *A61M 16/18* (2013.01); *A61M 2016/0027* (2013.01); *A61M 2016/1035* (2013.01); *A61M 2205/07* (2013.01); *A61M 2205/10* (2013.01); *A61M 2205/106* (2013.01); *A61M 2205/14* (2013.01); *A61M 2205/18* (2013.01); *A61M 2205/3317* (2013.01); *A61M 2205/3331* (2013.01); *A61M 2205/3341* (2013.01); *A61M 2205/3386* (2013.01); *A61M 2205/3569* (2013.01); *A61M 2205/3592* (2013.01); *A61M 2205/502* (2013.01); *A61M 2205/581* (2013.01); *A61M 2205/583* (2013.01)

(58) Field of Classification Search
 CPC .. A61M 12/14–147; A61M 12/18–186; A61M 12/20–209; A61M 2016/1035; A61M 2205/3341; F04B 49/06; F04B 49/08; F04B 17/03; F04B 53/12; F04B 9/1095; F04B 9/117; F04B 9/1295; F04B 9/137; F04B 23/02; F04B 23/025–026; A47K 5/1204; A47K 5/1205; A47K 5/1207; F17C 5/00–06; B65B 3/003; B65B 3/10; B65B 3/12; F25B 9/14
 See application file for complete search history.

(56) References Cited

U.S. PATENT DOCUMENTS

| | | | |
|---|---|---|---|
| 5,381,836 A | | 1/1995 | Braatz et al. |
| 5,427,145 A | | 6/1995 | Grabenkort |
| 5,505,236 A | | 4/1996 | Grabenkort et al. |
| 5,810,001 A | | 9/1998 | Genga et al. |
| 6,095,137 A | * | 8/2000 | Wallroth ............. A61M 16/104 |
| | | | 128/205.28 |
| 6,125,893 A | | 10/2000 | Braatz et al. |
| 6,138,672 A | | 10/2000 | Kankkunen |
| 6,171,276 B1 | | 1/2001 | Lippe et al. |
| 6,585,016 B1 | | 7/2003 | Falliggant et al. |
| 6,745,800 B1 | | 6/2004 | Sansom |
| 6,817,390 B2 | | 11/2004 | Falligant et al. |
| 6,878,133 B2 | | 4/2005 | Ahlmen et al. |
| 6,929,041 B2 | | 8/2005 | Falligant et al. |
| 7,290,571 B2 | | 11/2007 | Bunke et al. |
| 7,546,856 B2 | | 6/2009 | Chotenovsky |
| 7,886,780 B2 | | 2/2011 | Falligant et al. |
| 8,522,839 B2 | | 9/2013 | Freed et al. |
| 8,867,031 B2 | | 10/2014 | Jones et al. |
| 9,217,658 B2 | | 12/2015 | Kuehl et al. |
| 11,077,268 B2 | * | 8/2021 | Bender, II ........... A61M 16/183 |
| 2002/0069876 A1 | | 6/2002 | Loser et al. |
| 2006/0275165 A1 | * | 12/2006 | Wilke .................. B60T 8/4031 |
| | | | 417/553 |
| 2007/0034284 A1 | * | 2/2007 | Turker ................ A61M 16/183 |
| | | | 141/319 |
| 2007/0128048 A1 | | 6/2007 | Gonnella et al. |
| 2007/0169618 A1 | | 7/2007 | Scheller |
| 2009/0007913 A1 | * | 1/2009 | Lee ................... A61M 16/0072 |
| | | | 128/205.24 |
| 2009/0132094 A1 | | 5/2009 | Laverdiere et al. |
| 2009/0165787 A1 | | 7/2009 | Ahlmen et al. |
| 2010/0269820 A1 | | 10/2010 | Danielsen |
| 2012/0318263 A1 | | 12/2012 | Jones et al. |
| 2012/0318264 A1 | | 12/2012 | Jones et al. |
| 2013/0126464 A1 | | 5/2013 | Manzke et al. |
| 2013/0179046 A1 | | 7/2013 | Nassouri et al. |
| 2013/0287597 A1 | | 10/2013 | McNichol et al. |
| 2014/0193275 A1 | * | 7/2014 | Strobl .................... G01N 30/36 |
| | | | 417/12 |
| 2014/0378943 A1 | * | 12/2014 | Geipel ............. A61M 5/16809 |
| | | | 604/152 |
| 2015/0306339 A1 | | 10/2015 | Danielsen |
| 2016/0069344 A1 | | 3/2016 | Carey et al. |
| 2017/0122057 A1 | * | 5/2017 | Cowie ................ E21B 33/0355 |

FOREIGN PATENT DOCUMENTS

| | | |
|---|---|---|
| FR | 2570609 | 3/1986 |
| GB | 2181493 | 4/1987 |
| WO | 2000027458 | 5/2000 |
| WO | 2005056093 | 6/2005 |
| WO | 2007006348 | 1/2007 |
| WO | 2008151667 | 12/2008 |

\* cited by examiner

ANESTHESIA VAPORIZER RESERVOIR AND SYSTEM

CROSS REFERENCE TO RELATED APPLICATION

This application is a continuation of U.S. patent application Ser. No. 15/793,740, filed Oct. 25, 2017, which is incorporated herein by reference in entirety.

BACKGROUND

This disclosure generally relates to anesthesia vaporizer systems and reservoirs therefor that contain a pressured liquid anesthetic agent that is vaporized to deliver a gaseous anesthetic agent to a patient.

Anesthesia vaporizer systems are generally known and contain pressurized liquid anesthetic agent that is vaporized within the system and delivered to the patient as a gaseous anesthetic agent. Anesthesia vaporizer systems generally include a vaporizer reservoir that contains a liquid anesthetic agent to be delivered to the patient, a vaporizing unit or system that vaporizes the liquid anesthetic agent, and a delivery system that delivers the gaseous anesthetic agent to the patient. Various prior art systems utilize various vaporization methods, including pneumatic over hydraulic delivery systems, wicks that evaporate the anesthetic agent into a surrounding gas stream, or heating systems that heat the anesthetic agent to cause vaporization to be mixed with other gases for delivery to the patient.

Prior art systems often include at least two reservoirs, such as a secondary reservoir fluidly connected to a primary reservoir. The primary reservoir is generally pressurized in order to maintain the liquid anesthetic agent at a higher pressure than atmospheric pressure. When the anesthetic vaporizer system is to be filled or replenished with liquid anesthetic agent, the secondary reservoir is disconnected from primary reservoir and is operative to provide anesthetic agent to the patient during refilling of the primary reservoir with liquid anesthetic agent. When the primary reservoir is disconnected from the secondary reservoir, it is depressurized in order to bring the primary reservoir to atmospheric pressure, whereupon a liquid anesthetic agent source is poured into the primary reservoir. Once refilled, the driving pressure is restored in the primary reservoir, and the primary reservoir is reconnected to the secondary reservoir for continued operation.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, an anesthesia vaporizer system comprises a vaporizer reservoir forming a sump chamber that contains a liquid anesthetic agent, a piston in the vaporizer reservoir wherein the piston forms a first chamber within the vaporizer reservoir on a first side of the piston. The vaporizer reservoir further has a fill port configured to receive a refill container containing liquid anesthetic agent and to permit flow from an exterior of the vaporizer reservoir into the first chamber. A motor moves the piston between a first position within the vaporizer reservoir and a second position within the vaporizer reservoir wherein the volume of the first chamber increases as the piston moves from the first position towards the second position. The system is further configured such that as the piston moves from the first position toward the second position, the liquid anesthetic agent is drawn from the refill container into the first chamber. The system further includes a transfer valve configured to permit the liquid anesthetic agent to flow from the first chamber into the sump chamber, and an outlet port that delivers the liquid anesthetic agent from the sump chamber into a vaporizing system that vaporizes the liquid anesthetic agent for delivery to a patient.

In one embodiment, a vaporizer reservoir for an anesthesia vaporizer system includes a piston in the vaporizer reservoir, wherein the piston forms a first chamber at a first end of the vaporizer reservoir. The piston is movable along the length of the vaporizer reservoir between a first position and a second position, wherein the volume of the first chamber increases as the piston moves from the first position to the second position. The vaporizer reservoir further includes a fill port configured to receive a refill container of liquid anesthetic agent and a valve in the fill port configured to permit flow of the liquid anesthetic agent from an exterior of the vaporizer reservoir into the first chamber, wherein the system is configured such that as the piston moves from the first position towards the second position, the liquid anesthetic agent is draw from the refill container into the first chamber. The vaporizer reservoir further includes a sump chamber configured to contain liquid anesthetic agent, the sump chamber being at the second end of the vaporizer reservoir. The vaporizer reservoir further includes a transfer valve configured to permit the liquid anesthetic agent to flow from the first chamber into the sump chamber, and an outlet port that delivers the liquid anesthetic agent from the sump chamber to a vaporizing system that vaporizes the liquid anesthetic agent for delivery to a patient.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

Through their experimentation and research in the relevant field, the inventors have recognized a need for an improved vapor reservoir offering a faster and safer fill process that does not require depressurization of the reservoir. The inventors have recognized that many systems require the stoppage of anesthetic delivery during the fill process, or otherwise incorporate complicated systems and circuitry, such as that described above, to provide a secondary reservoir system for usage during the fill process. Such secondary systems introduce additional complication, cost, and points of failure into the system, and also require additional steps by a user that increase opportunity for error. Accordingly, the inventors have endeavored to develop an anesthesia vaporizer system comprising a single vaporizer reservoir that offers a fast refill process and/or is able to be refilled during continuous operation of the system to deliver the anesthetic agent to the patient.

The inventors have also recognized that current anesthesia vaporizer systems leak anesthetic agent into the surrounding environment during the fill process, such as when a refill container is poured in to the vaporizer reservoir and/or when the refill container is removed from the vaporizer reservoir after it has been emptied into the vaporizer reservoir. As currently available vaporizer reservoirs and system maintain positive pressure in the reservoir, a small amount of anesthetic agent leaks out of, or otherwise escapes from, the vaporizers reservoir and/or the refill container during the refill process. This is a known issue that has, heretofore, been considered unavoidable and thus permitted. Standards have been developed to regulate, yet permit, leakage of anesthetic agent during the refill the process. Such standards have been developed because ingestion of leaked anesthetic agent by healthcare personnel can cause drowsiness and may cause health issues, especially for such personnel who are pregnant or who have particular medical needs or conditions.

Figure 1:
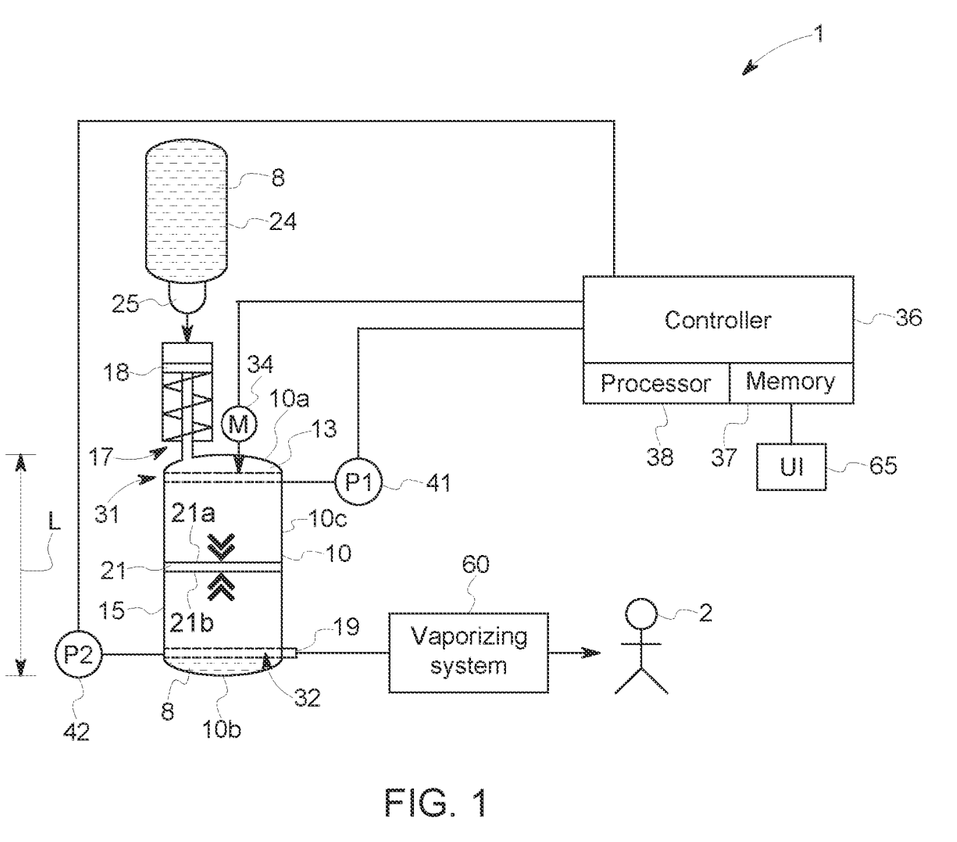
FIG. 1 provides a schematic depiction of an anesthesia vaporizer system according to the present disclosure.

In recognition of the foregoing challenges and problems, the inventors have endeavored to develop a vaporizer reservoir and associated anesthesia vaporizer system that eliminates leakage of anesthetic agent into the surrounding environment during the fill process. FIG. 1 is schematic diagram of an exemplary anesthesia vaporizer system 1. The system generally includes a vaporizer reservoir 10 that contains liquid anesthetic agent 8. The liquid anesthetic agent 8 is delivered from the vaporizer reservoir 10 to a vaporizing system 60, where it is converted to a gaseous anesthetic agent and delivered to the patient 2 in a controlled manner. The vaporizer reservoir 10 contains a piston 21 that pushes the liquid anesthetic agent 8 out of an outlet port 19 of the vaporizer reservoir 10, thus providing a piston over hydraulic delivery system of the liquid anesthetic agent 8. The piston 21 is movably sealed against the side walls 10c of the vaporizer reservoir 10, and thus creates a pressurized chamber, herein referred to as a sump chamber, that maintains the liquid anesthetic agent 8 under pressure.

The piston 21 is moved by a motor 34 within the vaporizer reservoir 10 between a first position 31 and a second position 32. Such movement adjusts the respective sizes of the chambers on either side of the piston 21. The piston 21 moves to the first position 31, which is at or near a first end 10a of the vaporizer reservoir 10. The piston 21 then moves down along the length L of the reservoir toward a second position 32 and a second end 10b of the vaporizer reservoir 10. As the piston 21 moves down along the length L of the vaporizer reservoir 10, the first chamber 13 defined by the piston 21 grows larger. The first chamber 13 is on a first side 21a of the piston 21, and the volume of that chamber increases as the piston 21 moves away from the first end 10a. As the volume of the first chamber 13 increases, the pressure of the sealed chamber decreases. The vacuum draws the anesthetic agent 8 out of the refill container 24, which is sealably connected to the vaporizer reservoir 10, and into the first chamber 13. The piston 21 is continually moved toward the second end 10b of the vaporizer reservoir 10 in order to draw in all of the liquid anesthetic agent 8 from the refill container 24. In the depicted embodiment, the refill container 24 is a bottle containing the liquid anesthetic agent 8, the bottle having a nozzle 25 configured to sealably mate with the fill port 17 of the vaporizer reservoir 10.

Beneficially, the disclosed vaporizer reservoir 10 offers a controlled and fast refill process whereby the piston 21 is utilized to draw liquid anesthetic agent 8 from a refill container 24 into the vaporizer reservoir 10 in a controlled manner. In one embodiment, the nozzle 25 is configured to be received within the fill port 17 and create a seal such that the vacuum within the first chamber 13 opens a fill valve 18 in the fill port 17 to permit the flow of the liquid anesthetic agent 8 from the refill container 24 into the first chamber 13. The fill valve 18 may also be configured to prevent any anesthetic agent from exiting the first chamber 13 as the refill container 24 is removed from the fill port 17. To provide just one exemplary embodiment, the fill valve 18 may be a check valve that opens when a vacuum is created in the first chamber so as to allow flow from the exterior of the vaporizer reservoir into the first chamber 13, but to disallow any flow of liquid or gaseous anesthetic agent out of the first chamber 13 to the exterior. In other embodiments, the fill valve 18 may be a spring valve that is opened when a refill container 24 is secured within the fill port 17.

Accordingly, as the first chamber 13 is at a vacuum pressure at the time that the refill container 24 is removed, or at least no greater than the external pressure of the vaporizer reservoir 10, the anesthetic agent will be prevented from escaping the first chamber 13 as the fill container is removed and as the fill valve 18 closes. This provides a significant safety benefit for clinicians over current systems which, as described above, permit at least some leakage of anesthetic agent during the refill process. Additionally, the vacuum between the first chamber 13 and the refill container 24 may act as an additionally securing mechanism to ensure that the refill container 24 remains securely connected to the vaporizer reservoir 10 during the refill process. This provides an additional safety benefit, as it reduces the possibility of leakage of anesthetic agent during the refill process due to the refill container 24 becoming accidentally disconnected or dislodged from the fill port 17 of the vaporizer reservoir 10.

The system further includes a controller 36 that controls a motor 34 in order to move the piston 21, such as to maintain a constant pressure on the liquid anesthetic agent 8. The controller 36 is communicatively connected to a user interface 65, which serves as a user input device through which a clinician can input patient information, control values, etc., and an output device that outputs patient information (such as physiological monitoring information), system function information, and alerts and alarms regarding the anesthesia system and/or the patient condition. The controller 36 receives information about the status in the vaporizer reservoir 10 from one or more sensors associated therewith, including pressure sensors sensing pressure of the various chambers within the vaporizer reservoir 10 and/or position sensors detecting a position of the piston 21 within the vaporizer reservoir 10.

The system 1 may include a first pressure sensor 41 sensing pressure within the first chamber 13 and providing such information to the controller 36. The controller 36 may then control the motor 34 moving the piston 21 based on such pressure measurements. For example, during a fill operation, the controller 36 may move the piston 21 in order to increase the volume of the first chamber 13 until a threshold pressure decrease or a threshold relative vacuum pressure (compared to the external pressure to the vaporizer reservoir 10) is sensed by the first pressure sensor 41 indicating that all of the liquid anesthetic agent 8 has been removed from the refill container 24.

Once the refill liquid anesthetic agent 8 is drawn into the first chamber 13 and the refill valve 18 is closed, the liquid anesthetic agent 8 is then transferred from the first chamber 13 to the sump chamber 15. In the sump chamber 15, the liquid anesthetic agent 8 is maintained at a defined pressure, which is greater than atmospheric pressure and the external pressure outside of the vaporizer reservoir 10. In various embodiments, the positive pressure may be exerted on the liquid anesthetic agent 8 by the piston 21 (see FIGS. 2A-2D) or by a second piston 22 (see FIGS. 4A-4D and 5). The liquid anesthetic agent 8 is moved from the first chamber 13 to the sump chamber 15 via a transfer valve 27 configured to permit the liquid anesthetic agent 8 to flow from the first chamber 13 to the sump chamber 15. Various types of valves and configurations may be utilized as the transfer valve 27, and various examples are provided herein. The transfer valve 27 may be within the vapor reservoir 10 or may be outside of the vapor reservoir 10.

Figure 2A:
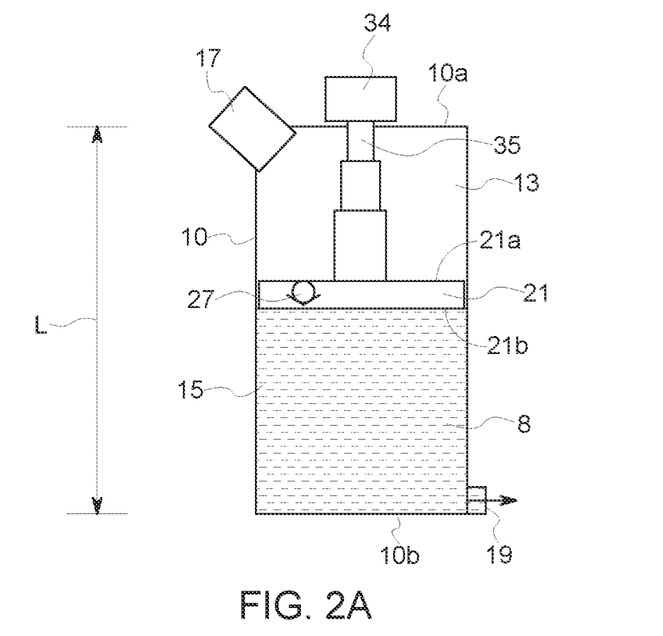
FIGS. 2A-2D schematically depict a vaporizer reservoir and associated fill process according to one embodiment of the disclosure.

FIGS. 2A-2D depict one embodiment of a vapor reservoir 10 and associated fill process. In the depicted embodiment, the piston 21 divides the first chamber 13 from the sump chamber 15, wherein the first chamber 13 is on a first side 21a of the piston 21 and the sump chamber 15 is on a second side 21b of the piston 21. As the piston 21 moves up and down within the vapor reservoir 10 the volume of the first chamber 13 and the sump chamber 15 change accordingly. In FIG. 2A, the vaporizer reservoir 10 is approximately half full of the liquid anesthetic agent 8. Thus, the piston 21 is approximately in the middle of the vaporizer reservoir 10, with the first chamber 13 on top (adjacent to the first side 21a) and the sump chamber 15 below (adjacent to the second side 21b) the piston 21. The piston applies pressure to the liquid anesthetic agent 8, which forces the liquid anesthetic agent 8 out of the outlet port at the same pressure. The liquid anesthetic agent is provided from the outlet port 19 to the vaporizing system 60, and then delivered to the patient. The piston 21 is moved down the length L of the chamber accordingly, meanwhile maintaining the liquid anesthetic agent 8 under constant pressure.

Once the liquid anesthetic agent within the vaporizer reservoir 10 gets low, the fill process may be initiated. If the refill process is not initiated, the piston 21 continues until it reaches the second position 32, which may be an absolute minimum location at or near the second end 10b of the vaporizer reservoir 10. In certain embodiments like that schematically shown in FIG. 1, the outlet port 19 is positioned such that when the piston 21 reaches the second position 32 it blocks or closes off the outlet port 19 such that no more anesthetic agent can be delivered therethrough.

Once the refill process is instructed, such as by the clinician via the user interface 65, the piston 21 is moved upward to the first position 31 near the top, or first end 10a, of the vaporizer reservoir 10. Such state is exemplified at FIG. 2B. A refill container 24 is then connected to the fill port 17. In certain embodiments, a sensor may be positioned within the fill port 17 or within the first chamber 13 to detect when a refill container 24 is securely sealed to the fill port 17. Downward movement of the piston 21 may be automatically initiated by the controller 36, or permitted to be initiated by a user, once the refill container 24 is secured to the fill port 17.

Figure 2B:
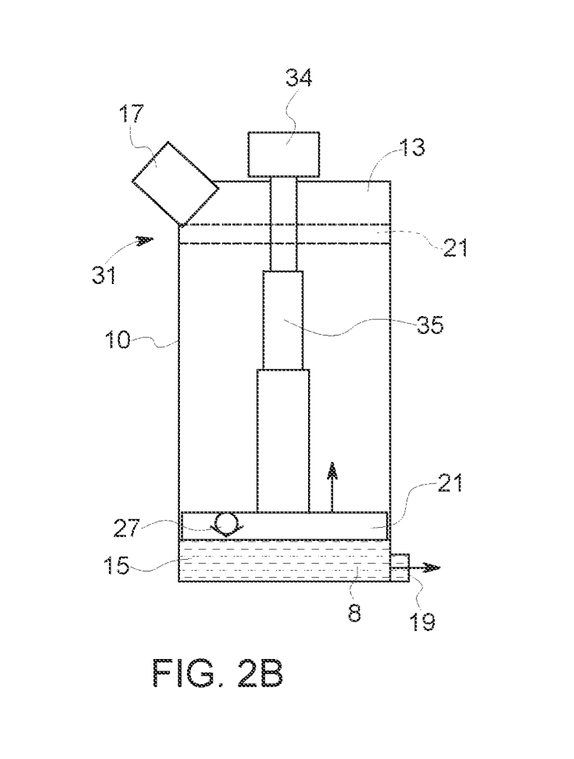
Figure 2C:
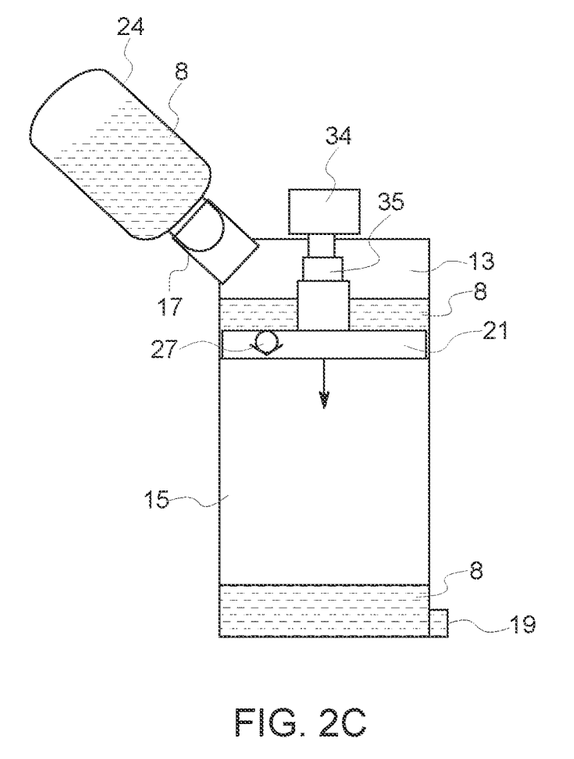

As illustrated in FIG. 2C, the piston 21 is then moved down along the length L of the chamber, drawing the liquid anesthetic agent 8 out of the refill container 24 and into the first chamber 13 above the piston 21. The piston 21 is controlled so as to continually move down the length L of the vapor reservoir 10 until all liquid anesthetic agent 8 is pulled from the refill container 24 into the first chamber 13.

At that point, the refill container 24 is removed from the fill port 17. As described above, a fill valve 18 may be provided in the fill port 17 that prevents any anesthetic agent from escaping from the first chamber 13. For example, if the first chamber 13 is at a vacuum pressure compared to the external pressure at the time that the fill container 24 is removed, anesthetic agent will be prevented from escaping the first chamber 13 as the fill container is removed and the fill valve 18 closes.

The liquid anesthetic agent 8 in the first chamber 13 is then moved into the sump chamber 15. As exemplified in the schematic at FIG. 2D, the piston 21 is moved upward toward the first end 10a of the vaporizer reservoir 10. The transfer valve 27 is also opened to allow the flow of liquid anesthetic agent 8 from the first chamber 13 through the transfer valve 27 to the sump chamber 15. In the depicted embodiment, the transfer valve 27 is located in the piston 21 head. In one exemplarily embodiment, the transfer valve 27 may be a check valve that opens when downward pressure is exerted thereon by the liquid anesthetic agent 8 in the first chamber 13. In certain embodiments, the transfer valve 27 may be configured to automatically open when pressure is applied thereon from the upward motion of the piston 21, which increases the pressure within the first chamber 13.

Figure 2D:
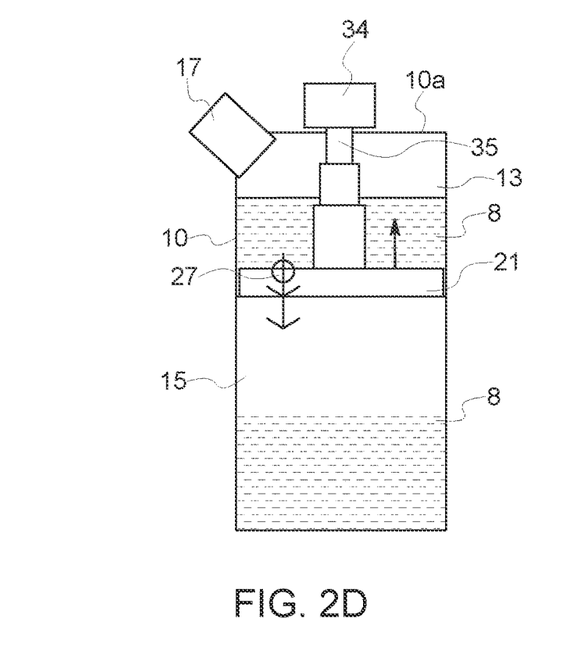

Once all of the liquid anesthetic 8 is transferred to the sump chamber 15, the piston 21 is moved into a position in order to apply the predetermined constant pressure on the liquid anesthetic agent 8 in the sump chamber 15. Accordingly, the above discussed fill process may require cessation of delivery of the anesthetic agent to the patient during the fill process. However, the fill process can occur quite quickly, as it is primarily defined by how quickly the piston 21 is moved to execute the foregoing steps.

Figure 3A:
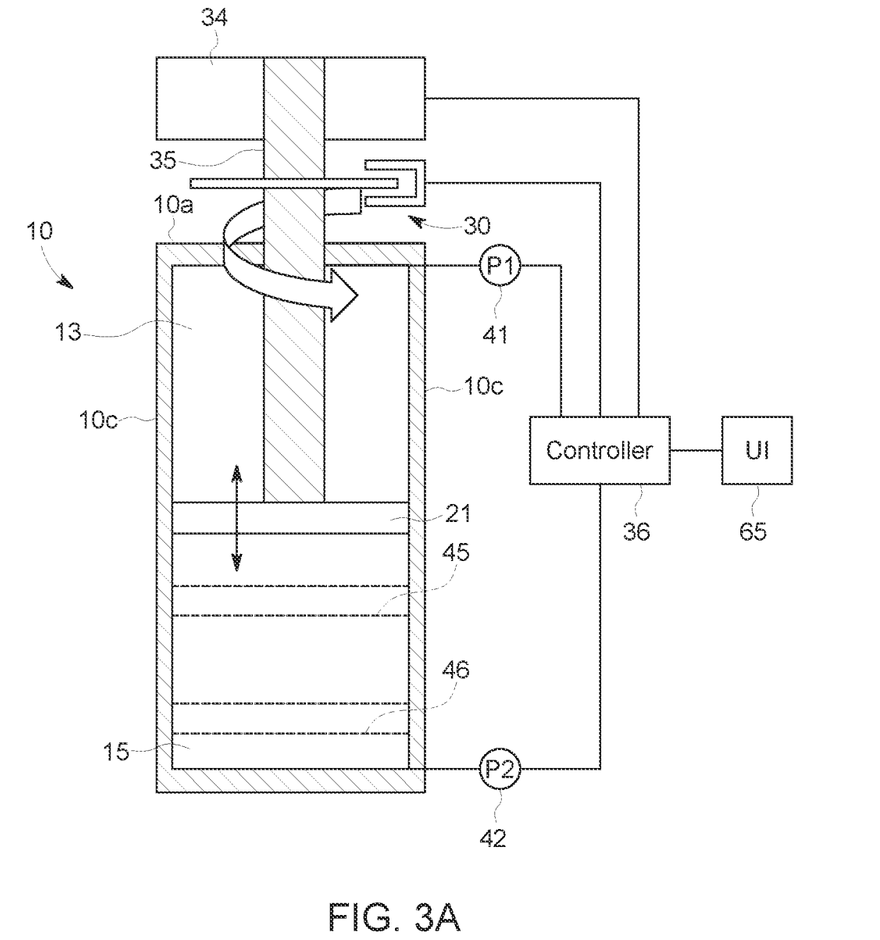
FIGS. 3A-3B schematically depict additional embodiments of vaporizer reservoir arrangements for inclusion in anesthesia vaporizer systems.

A motor 34 is operatively connected to the piston 21 so as to move the piston 21 as needed for the refill process and/or for maintenance of the constant pressure in the sump chamber 15. In one embodiment, the motor 34 is a stepper motor that engages a lead screw 35 connected to the piston 21. Thus, the stepper motor 34 moves the piston 21 by turning the lead screw 35 clockwise or counterclockwise. As depicted in FIGS. 2A-2C, the lead screw 35 may be telescopic lead screw. In other embodiments, the lead screw 35 may be a straight unitary lead screw as schematically depicted in FIG. 3A. In one embodiment, the stepper motor 34 is housed externally to the vaporizer reservoir 10, and the lead screw 35 extends through a housing of the vaporizer reservoir 10, such as through a first end 10a. A rotary seal is provided around the lead screw 35 where it extends through the vaporizer reservoir 10. In one embodiment, the piston 21 is rotated by the lead screw 35, and thus the seal between the piston 21 and the side walls 10c of the vaporizer reservoir 10 is also a rotary seal. In another embodiment, the piston 21 head may move linearly up and down the lead screw 35, thus requiring a rotary seal between the piston 21 head and the lead screw 35.

Figure 3B:
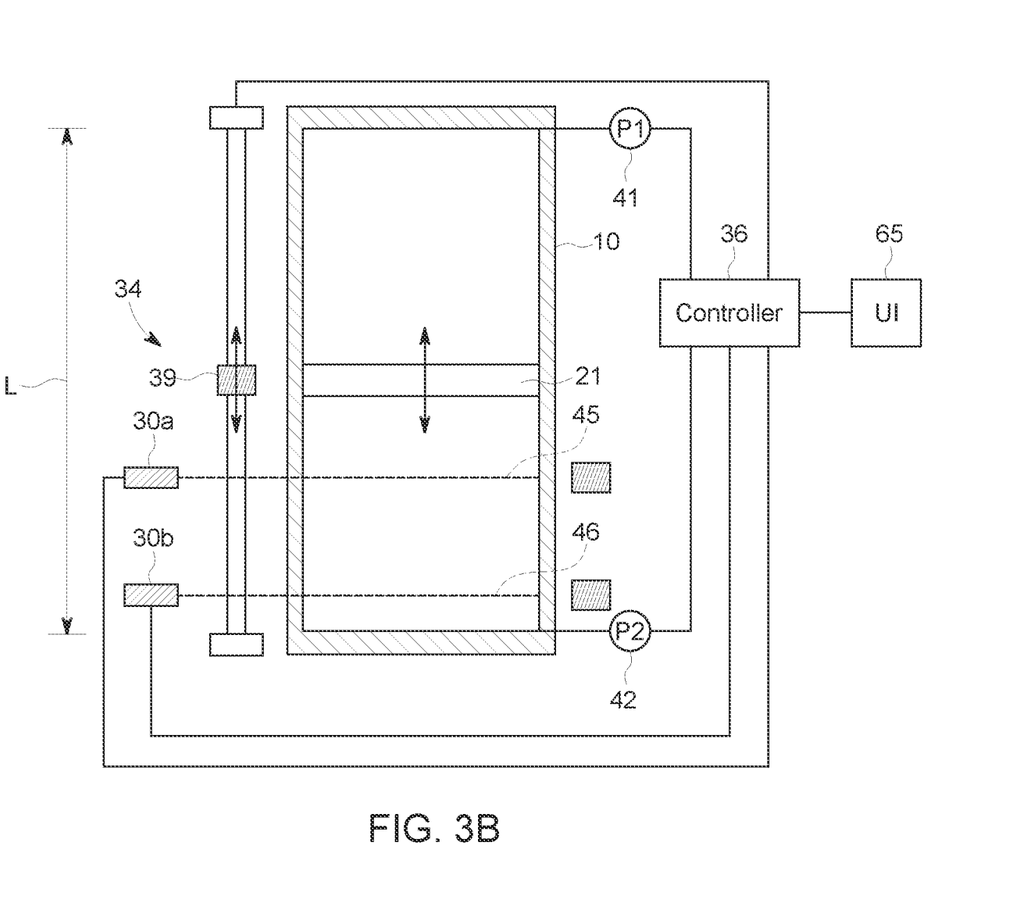

In other embodiments, the motor 34 may move the piston 21 by other means. In one embodiment exemplified in FIG. 3B, the motor 34 may be a linear motor that magnetically moves the piston 21 up and down along the length L of the vaporizer chamber 10. In such an embodiment, the piston 21 may be comprised of a ferrous material having magnetic properties, such as steel, while the housing of the vaporizer reservoir may be comprised of a non-ferrous material, such as aluminum. The linear motor 34 moves the piston 21 by moving a magnetic field to attract the piston 21 in one direction or another. In one embodiment, the magnetic motor 34 may comprise a magnet 39 that is moved along the length L of the vaporizer reservoir 10, or at least between a first position 31 and a second position 32 defining a range of movement of the piston 21. In other embodiments, the magnetic field may be generated by exciting a rail, or coil, extending width wise around the vaporizer reservoir 10. The coils are then strategically energized, thereby creating a movable magnetic field that acts to move the piston 21 in accordance with commands from the controller 36. This linear motor embodiment has the benefit of being able to control the piston 21 without physical contact thereto, and thus avoiding the problems relating to rotary or other seals at locations where elements extend through the housing of the vaporizer reservoir 10.

One advantage of the disclosed piston over hydraulic system for delivery and managing liquid anesthetic agent 8 in the vaporizer reservoir 10 is that the position of the piston provides mechanical feedback as to the amount of liquid anesthetic agent 8 in the vaporizer reservoir 10 or at least in the sump chamber 15, thus allowing for precisely controlled and highly accurate anesthetic delivery. Accordingly, a piston position sensor 30 may sense the current position of the piston 21 in order to determine the amount of liquid anesthetic agent 8 currently available in the vaporizer reservoir 10.

In the above-described lead screw embodiment, the piston position sensor 30 may include a rotary encoder determining the rotational position of the lead screw 35, and thereby determining the position of the piston 21. In such an embodiment, exemplified in the schematic diagram at FIG. 3A, the rotary encoder 30 provides the rotational position of the lead screw 35 to the controller 36, which then interprets the position of the piston 21 accordingly. For example, the rotary encoder input may be provided as feedback for controlling the stepper motor 34. Additionally, the position information from the rotary encoder 30 may be used by the controller 36 to determine whether a refill alert or empty alert should be generated to prompt a user to refill the vaporizer reservoir 10. For example, the controller 36 may store one or more predetermined positions that trigger alert generation. In the depicted example, a piston location associated with a refill position 45 within the vaporizer reservoir 10 may be recognized by the controller 36. Upon detecting position information from the rotary encoder piston position sensor 30 indicating that the piston 21 (or piston 22 in the embodiments at FIGS. 4A-4D) is at the refill position 35, the controller 36 may instruct generation of a first alert, such as a warning to the user that the liquid anesthetic agent 8 is getting low and should be refilled. Such an alert may be generated, for example, via the user interface 65 and may include a visual alert on a display screen and/or an audio alert via a speaker. Similarly, other positions may be stored within the controller 36, and alerts generated accordingly. For example, the controller 36 may generate a second alert when the piston 21 reaches an empty position 46, such as an alert on the user interface 65 to prompt a user to immediately refill the vaporizer reservoir 10.

The controller 36 may further receive pressure information about the vapor reservoir 10 from one or more pressure sensors 41, 42 sensing pressure at various locations within the vapor reservoir 10. For example, the controller 36 may control the piston 21 based on pressure readings from a pressure sensor 42 in the sump chamber 15 so as to control the position of the piston 21 in order to maintain a constant pressure within the sump chamber 15. Thus, as liquid anesthetic agent is delivered out of the outlet port 19, the piston 21 is moved downward to decrease the volume of the sump chamber 15 in order to maintain a constant pressure therein.

In an embodiment where a linear motor 34 moves the piston 21, the system may include one or more piston position sensors 30 that are electromagnetic proximity sensors sensing the location of the magnetic field controlling the position of the piston 21. As exemplified in the schematic at FIG. 3B, a first electromagnetic proximity sensor 30a may be positioned to determine when the piston 21 is at the refill position 45, and a second electromagnetic proximity sensor 30b may be positioned to determine when the piston 21 is at the empty position 46. Alerts may be generated accordingly, as described above. For example, a first alert, such a refill warning, may be generated via the user interface 65 when the piston 21 is between the first electromagnetic proximity sensor 30a at the refill position 45, referred to herein as the refill proximity sensor, and the second electromagnetic proximity sensor at the empty position 46, referred to herein as the empty proximity sensor. In various embodiments, the refill proximity sensor 30a and the empty proximity sensor 30b may be any type of electromagnetic proximity sensor, including capacitive or inductive proximity sensors. As described above, the position information sensed by the proximity sensors 30a, 30b is provided to the controller 36, which may utilized such information to generate alerts to a user and/or as feedback for controlling the motor 34 to control the location of the piston 21.

The controller 36 communicates with each of the one or more components of the system 1 via one or more communication links, which can be any wired or wireless links employing any available communication protocol. The controller 36 is capable of receiving information and/or controlling one or more operational characteristics of the system 1 and its various sub-systems by sending and receiving control signals via the communication links. The controller 36 generally includes a processing system including at least one processor 38, and a storage system including memory 37. The controller 36 may further include a communication interface (not shown) for interfacing between the processing system, memory system, and/or one or more other elements within the system 1, including the position sensors 30, pressure sensors 41, 42, motor 34, user interface devices 65, etc. The processor 38 loads and executes software from memory 37 in order to carry out the functions and processes described herein. The system 1 may be implemented with one or more computer programs executed by one or more processors 38, which may all operate as part of a single controller 36. The computer programs include processor-executable instructions that are stored in memory 37 comprising a non-transitory tangible computer readable medium. Non-limiting examples of the non-transitory tangible computer readable medium are nonvolatile memory, magnetic storage, and optical storage. The computer programs may also include stored data.

Figure 4A:
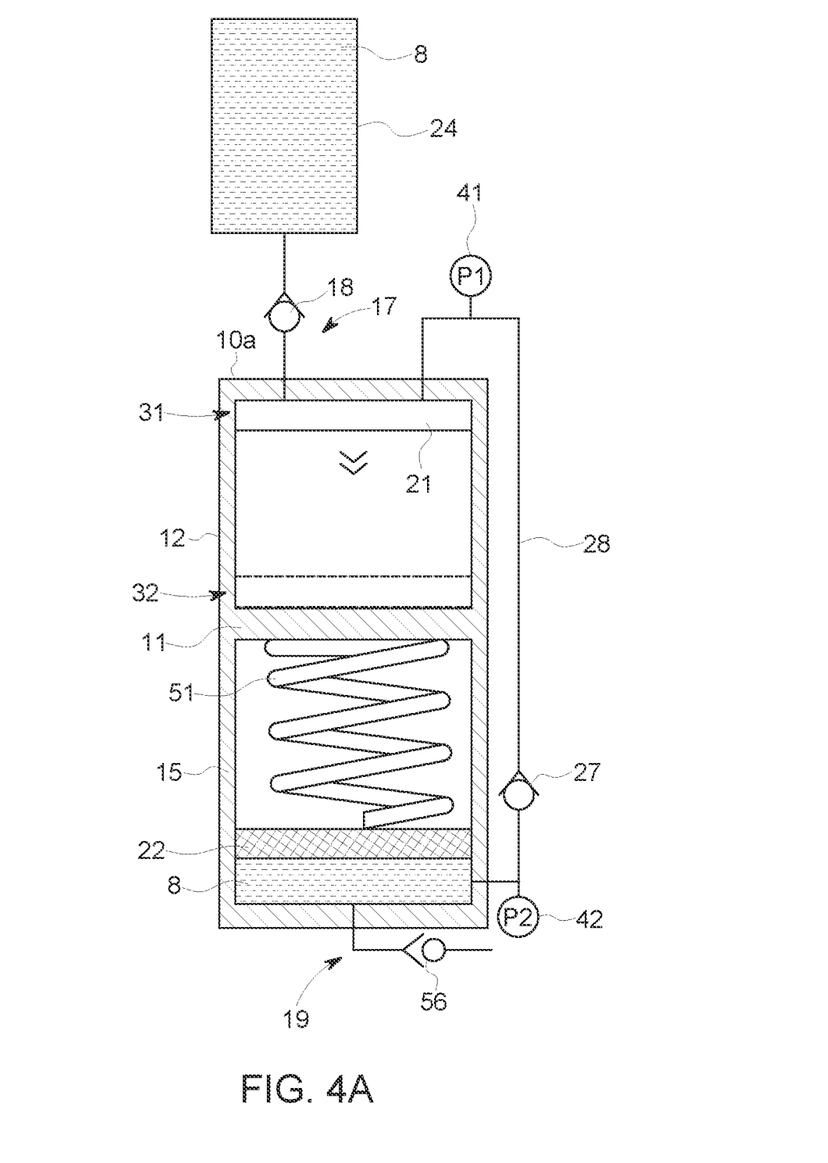
FIGS. 4A-4D provide a schematic depiction of an additional embodiment of a vapor reservoir and an associated fill process.

FIGS. 4A-4D and FIG. 5 depict another embodiment of the vaporizer reservoir 10 wherein a stationary divider 11 separates a fill chamber 12, which contains the first chamber 13. The stationary divider 11 completely isolates the sump chamber 15 from the fill chamber 12, thus allowing the refill process to occur without interruption of continuous delivery of the liquid anesthetic agent 8 from the sump chamber 15. The piston 21 operates in the refill chamber 12 to control the volume in the first chamber 13 in order to draw liquid anesthetic agent 8 out of a refill container 24, as is described above. Accordingly, the piston 21 moves between a first position 31 at the top of the refill chamber 12 and a second position 32 at the bottom of the refill chamber 12, as shown in FIG. 4A.

The sump chamber contains a second piston 22 exerting a constant pressure on the liquid anesthetic agent 8 therein. In the depicted embodiment, a constant spring 51 exerts a constant force on the second piston 22, which places the liquid anesthetic agent in the sump chamber 15 under constant pressure. The second piston 22 forces the anesthetic agent out of the outlet port 19 at the constant pressure. The outlet port 19 may include an outlet valve 56 that regulates the flow of liquid anesthetic agent. The outlet valve 56 may be, for example, a proportional valve.

Figure 5:
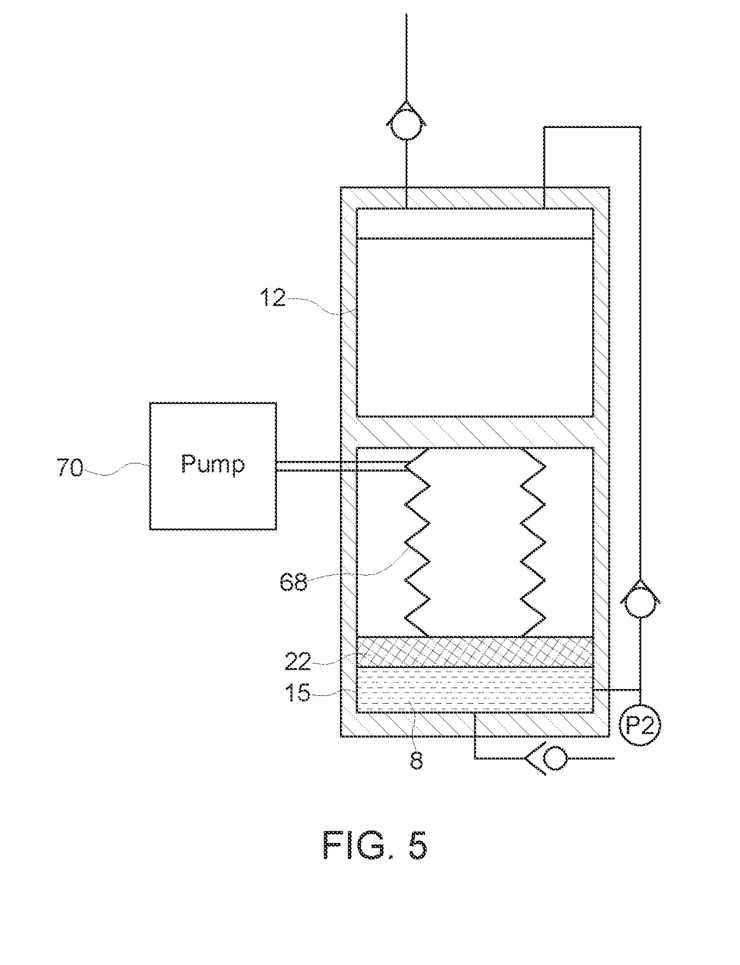
FIG. 5 schematically depicts an additional embodiment of a vapor reservoir.

FIG. 5 depicts another embodiment where the constant force exerted on the second piston 22 is provided by an air bladder 68. The air bladder 68 is inflated or deflated by pump 70 in order to maintain a constant force on the piston 22. For example, the pump 70 may be controlled to maintain a constant pressure within the air bladder 68. Thereby, a constant pressure is maintained on the liquid anesthetic agent 8 within the sump chamber 15.

Figure 4B:
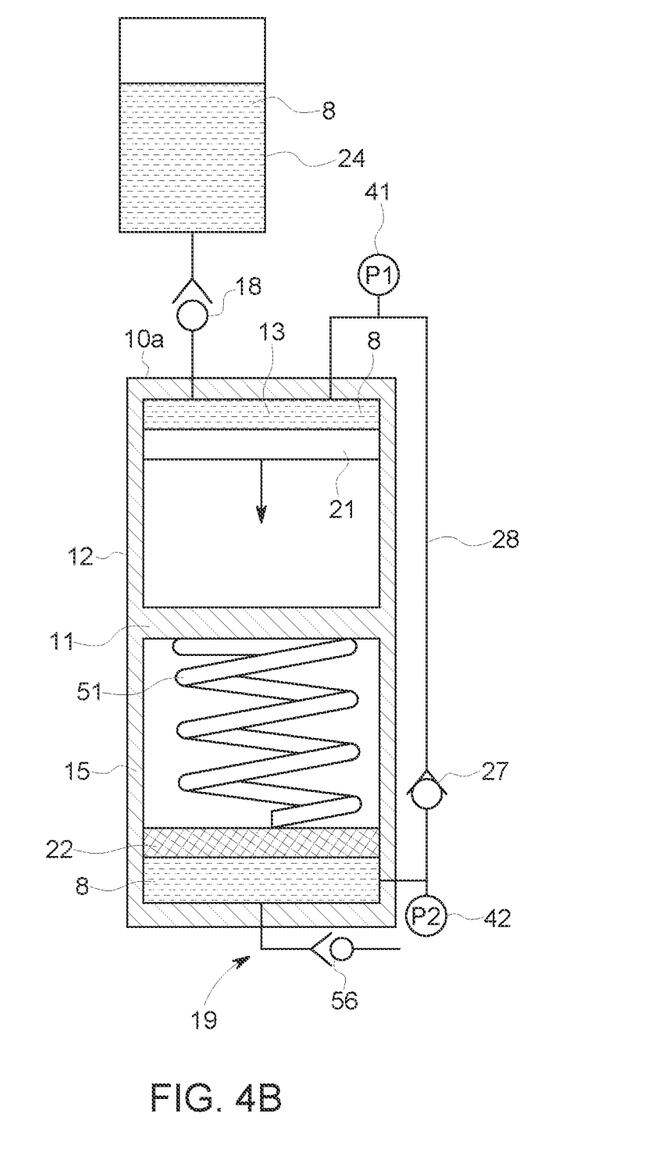
Figure 4C:
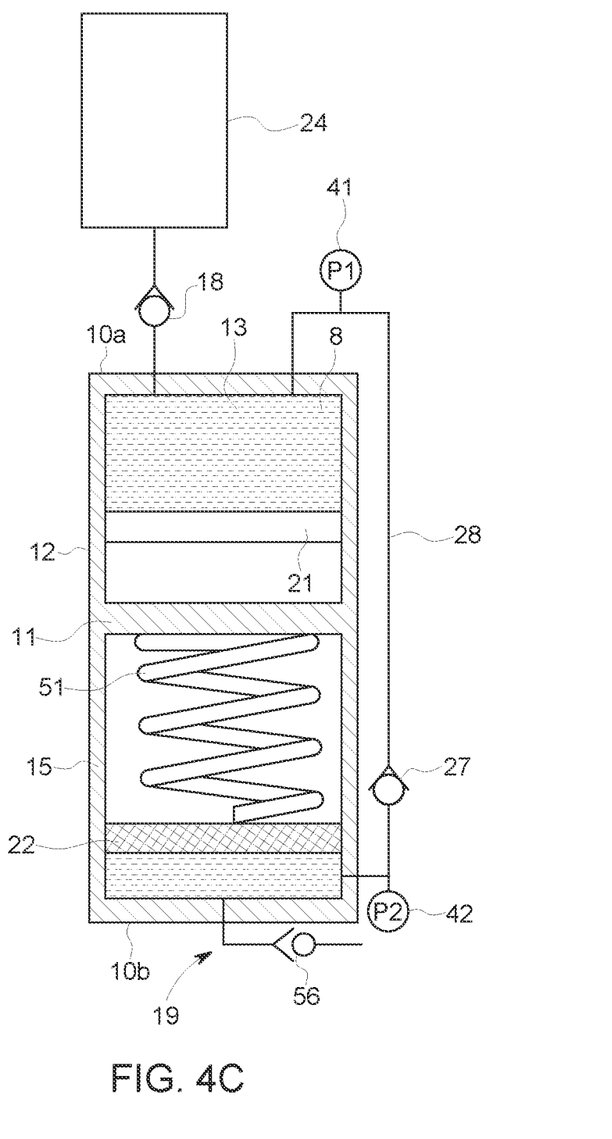

As depicted in FIGS. 4A-4D, the fill process is carried out while continually delivering liquid anesthetic agent from the sump chamber 15. In FIG. 4A, the liquid anesthetic agent 8 in the sump chamber 15 is low, such as at or below the refill position 45. Thus, a refill process is initiated, where the piston 21 is positioned at the first position 31, which in the depicted embodiment is at the top of the refill chamber 12. A full refill container 24 is provided, which is then connected to the refill port 17. Once the refill container 24 is securely positioned to create a seal with the fill port 17, the piston 21 is moved downward along the length of the fill chamber 12. The fill valve 18 is opened allowing liquid anesthetic agent 8 to flow into the first chamber 13 created as the piston 21 moves downward. In certain embodiments, the suction pressure created by the downward movement of the piston 21 opens the fill valve 18, such as where the fill valve 18 is a check valve. In other embodiments, the fill valve 18 may be a controllable valve switched open by the controller 36. FIG. 4B demonstrates this portion of a process, where liquid anesthetic agent 8 is being transferred from the refill container 24 through the fill valve 18 into the first chamber 13 as the piston 21 is moved downward.

Pressure sensor 41 continually measures pressure within the first chamber 13. Once all of the liquid anesthetic agent 8 is removed from the fill container 24, the pressure sensor P1 senses a pressure decrease. For example, once a threshold pressure decreased is sensed, the downward motion of the piston 21 may be stopped. Alternatively, the piston 21 may be stopped when a threshold negative pressure is sensed as compared to atmospheric pressure or the external pressure outside of the vaporizer reservoir 10. Once the liquid anesthetic agent is transferred to the first chamber 13, the valve 18 is closed and the fill container 24 is removed from the fill port 17 (see FIG. 4C). In certain embodiments, the valve 18 may be closed when the fill container 24 is removed. In other embodiments, the fill valve 18 closes when the vacuum pressure falls below the designed opening pressure.

Figure 4D:
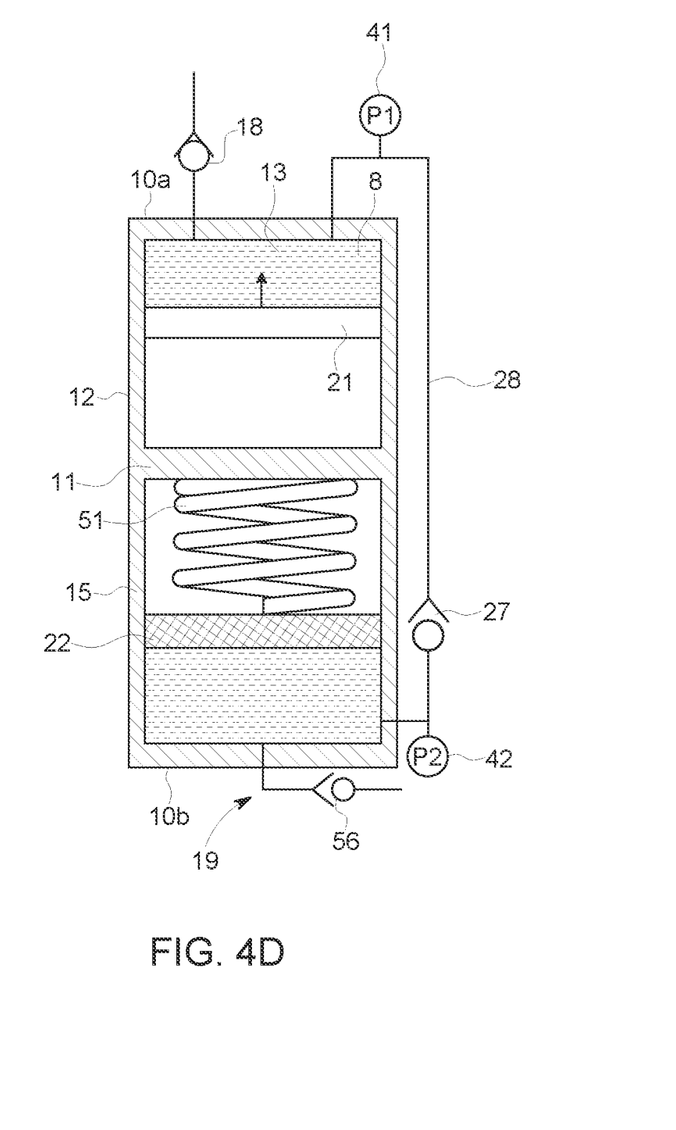

As illustrated in FIG. 4D, the liquid anesthetic agent 8 in the first chamber 13 is then transferred to the sump chamber 15 via the transfer valve 27 and the transfer tube 28. Specifically, the piston 21 is moved upward toward the top side 10a of the fill chamber 12 forcing the liquid anesthetic agent 8 out of the first chamber 13 through the transfer tube 28. Flow of the anesthetic agent 8 through the transfer tube 20a is controlled by the transfer valve 27, which is opened during the transfer process. For example, the transfer valve 27 may be a check valve that opens under a predetermined pressure, and such opening pressure is overcome when the piston 21 is moved upward. Accordingly, the liquid anesthetic agent 8 is transferred from the first chamber 13 into the sump chamber 15, where it will be delivered to the patient. Such fill process and transfer occurs without disrupting the continuous pressure in the sump chamber 15, and thus allowing for continuous delivery of anesthetic agent to the vaporizing system 60.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

We claim:

1. An anesthesia vaporizer system comprising:
a vaporizer reservoir forming a sump chamber that contains liquid anesthetic agent and a fill chamber isolated from the sump chamber configured to receive liquid anesthetic agent from a refill container;
a sump piston in the sump chamber configured to maintain an unchanging force on the liquid anesthetic agent in the sump chamber;
a transfer valve configured to permit the liquid anesthetic agent to flow from the fill chamber to the sump chamber; and
an outlet port that delivers the liquid anesthetic agent from the sump chamber to a vaporizing system that vaporizes the liquid anesthetic agent for delivery to a patient.

2. The system of claim 1, further comprising a stationary divider in the vaporizer reservoir isolating the fill chamber from the sump chamber.

3. The system of claim 1, further comprising a fill piston in the fill chamber configured to move between a first position and a second position, wherein as the fill piston moves from the first position toward the second position the liquid anesthetic agent is drawn from the refill container into the fill chamber.

4. The system of claim 3, wherein the system is configured such that as the fill piston moves from the second position toward the first position, the liquid anesthetic agent is forced out of the fill chamber through the transfer valve to the sump chamber.

5. The system of claim 3, wherein the fill piston is configured to maintain a vacuum in the fill chamber during refill so as to prevent any anesthetic agent from exiting the fill chamber as the refill container is removed from a fill port on the vaporizer reservoir.

6. The system of claim 3, further comprising a pressure sensor in the fill chamber;
wherein the sump piston is controlled such that movement of the sump piston is stopped when the pressure sensor senses a threshold pressure decrease.

7. The system of claim 1, further comprising a tube external to the vaporizer reservoir and communicating between the fill chamber and the sump chamber, and wherein the transfer valve is connected to the tube and configured to control flow of the liquid anesthetic agent from the fill chamber to the sump chamber.

8. The system of claim 1, further comprising a piston position sensor that senses a position of the sump piston within the sump chamber.

9. The system of claim 8, further comprising:
a refill proximity sensor and an empty proximity sensor each configured to sense position of the sump piston in the sump chamber;
a controller configured to generate a first alert via a user interface when the sump piston is between the refill proximity sensor and the empty proximity sensor and generates a second alert when the sump piston is at or below the empty proximity sensor.

10. The system of claim 1, further comprising a constant spring exerting the constant force on the sump piston as it moves within the sump chamber.

11. The system of claim 1, further comprising an air bladder exerting the constant force on the sump piston as it moves within the sump chamber.

12. The system of claim 11, further comprising a pressure sensor in the sump chamber sensing pressure on the liquid anesthetic agent from the sump piston, wherein inflation of the air bladder is controlled based on the sensed pressure.

13. The system of claim 12, wherein the system is configured such that the liquid anesthetic agent is continuously delivered from the sump chamber to the vaporizing system while the liquid anesthetic agent is drawn from the refill container into the fill chamber, and while the liquid anesthetic agent flows from the fill chamber into the sump chamber.

14. The system of claim 1, further comprising a fill port on the vaporizer reservoir configured to receive the refill container containing liquid anesthetic agent; a valve in the fill port configured to permit flow of the liquid anesthetic agent from an exterior of the vaporizer reservoir into the fill chamber.

15. The system of claim 1, further comprising a controller configured to control the sump piston to maintain the unchanging force on the liquid anesthetic agent to continuously deliver the liquid anesthetic agent through the outlet port.

16. A vaporizer reservoir for an anesthesia vaporizer system, the vaporizer reservoir having a length between a first end and a second end, the vaporizer reservoir comprising:
a sump chamber that contains liquid anesthetic agent;
a fill chamber configured to receive liquid anesthetic agent from a refill container;
a sump piston in the sump chamber configured to maintain an unchanging force on the liquid anesthetic agent therein;
a transfer valve configured to permit the liquid anesthetic agent to flow out of the fill chamber to the sump chamber; and
an outlet port that delivers the liquid anesthetic agent from the sump chamber to a vaporizing system that vaporizes the liquid anesthetic agent for delivery to a patient.

17. The vaporizer reservoir of claim 16, further comprising a stationary divider in the vaporizer reservoir isolating the fill chamber from the sump chamber.

18. The vaporizer reservoir of claim 16, further comprising a fill piston in the fill chamber configured to move between a first position and a second position, wherein as the fill piston moves from the first position toward the second position the liquid anesthetic agent is drawn from the refill container into the fill chamber.

19. The vaporizer reservoir of claim 18, wherein the anesthesia vaporizer system is configured such that as the fill piston moves from the second position toward the first position, the liquid anesthetic agent is forced out of the fill chamber through the transfer valve to the sump chamber.

20. The vaporizer reservoir of claim 16, wherein the anesthesia vaporizer system is configured to maintain a vacuum in the fill chamber so as to prevent any anesthetic agent from exiting the fill chamber as the refill container is removed from the fill port.

21. The vaporizer reservoir of claim 16, further comprising a constant spring or an air bladder exerting the constant force on the sump piston as it moves within the sump chamber.

* * * * *